(12) United States Patent
Rodov

(10) Patent No.: US 6,697,837 B1
(45) Date of Patent: Feb. 24, 2004

(54) END USER PROFILING METHOD

(75) Inventor: Alexander G Rodov, Hoffman Estates, IL (US)

(73) Assignee: Installation Software Technologies, Inc., Schaumburg, IL (US)

( * ) Notice: Subject to any disclaimer, the term of this patent is extended or adjusted under 35 U.S.C. 154(b) by 0 days.

(21) Appl. No.: 09/444,242

(22) Filed: Nov. 19, 1999

(51) Int. Cl.[7] .............................................. G06F 15/177
(52) U.S. Cl. ....................... 709/203; 709/220; 717/178
(58) Field of Search ................................. 709/220, 221, 709/222, 203, 202, 207; 717/168, 172, 173, 174, 176, 177, 178

(56) References Cited

U.S. PATENT DOCUMENTS

| | | | | |
|---|---|---|---|---|
| 5,588,148 A | * | 12/1996 | Landis et al. ................... | 707/1 |
| 5,752,042 A | * | 5/1998 | Cole et al. .................... | 717/173 |
| 5,771,381 A | * | 6/1998 | Jones et al. ................... | 713/100 |
| 6,029,196 A | * | 2/2000 | Lenz ........................... | 709/221 |
| 6,347,331 B1 | * | 2/2002 | Dutcher et al. ............. | 709/203 |

* cited by examiner

*Primary Examiner*—Dung C. Dinh
(74) *Attorney, Agent, or Firm*—Kajane McManus

(57) ABSTRACT

The method is provided for creating, transmitting, extracting and storing an end user profile on the end user's computer which is reaccessible and comprises the steps of: determining if a profile for the end user exists on the website server and if not; polling the end user and obtaining input desired for creating the profile on the server; creating the profile; embedding a copy of the profile into an action tag pointing to a download package through a data filter on a server; generating a download package comprising the desired data and a profile extraction program; generating an HTML page including the action tag for actuation by the user for downloading selected data; upon execution of the action tag by the user beginning operation of the data filter to transfer the user profile from the tag into the download package and downloading the package; upon opening of the package running the extraction program to extract the profile from the download package and saving the profile to a predetermined file location on the end user's computer; and accessing the profile as needed for eliminating rekeying by the user of profile information contained therein.

14 Claims, 3 Drawing Sheets

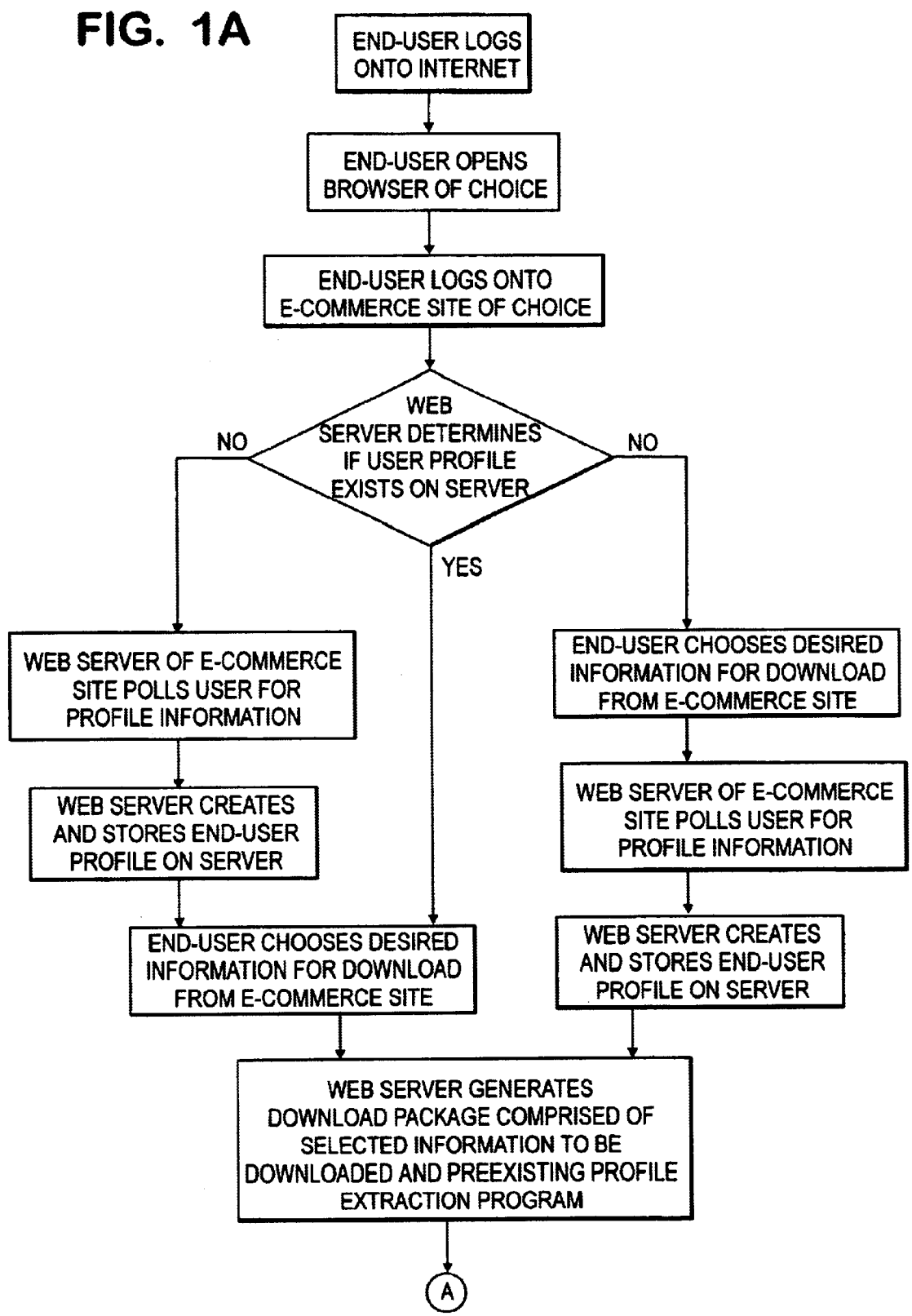

END USER PROFILING METHOD

BACKGROUND OF THE INVENTION

1. Field of the Invention

The invention relates to a method of creating and storing a reaccessible, browser independent end user profile on the end user's computer, at least upon initial access, of an e-commerce website offering the purchase, downloading and installation of software or information (data) therefrom, without requiring the user to repeatedly enter the profile information. More specifically, the end user profile is downloaded and stored invisibly and seamlessly with the desired data download from the website.

2. Description of the Prior Art

Heretofore, end user profiling has been accomplished in a more or less program specific manner.

As an example, when a user on the internet accesses a site for download of desired data therefrom, the user must use a specific browser (of choice) to gain access to the site. A typical browser incorporates a function which creates and stores, from input end information, an end user profile in a particular area on the end use's computer, with the information only being retrievable by the particular browser used when creating the profile. One easily recognized form of such browser dependent function is commonly referred to as a cookie.

Thus, if a user switches between browsers, access to the end user profile by the new browser selected is impossible.

Further, programming is available which will not allow creation of cookies, requiring repeated user information input upon each access of any site requiring user profiling before access is allowed, or upon installation of an application necessary for retrieval of the download data, if such application requires a profile as well.

SUMMARY OF THE INVENTION

Accordingly there is a need in the industry for a method of creating and storing a reaccessible end user profile on the end user's computer which is independent of the browser selected for use by the end user.

Further, there is a need for such method to be accomplished in a substantially seamless manner invisible to the end user, with the end user profile being transferred and stored in a predetermined generically accessible location on the end user's computer, such as in the registry of the operating system in use.

These, as well as other objects are met by the method described in detail hereinafter.

BRIEF DESCRIPTION OF THE DRAWING

The FIGURE is an operational flow chart of the method of the present invention.

DESCRIPTION OF THE PREFERRED EMBODIMENT

Figure 1B:
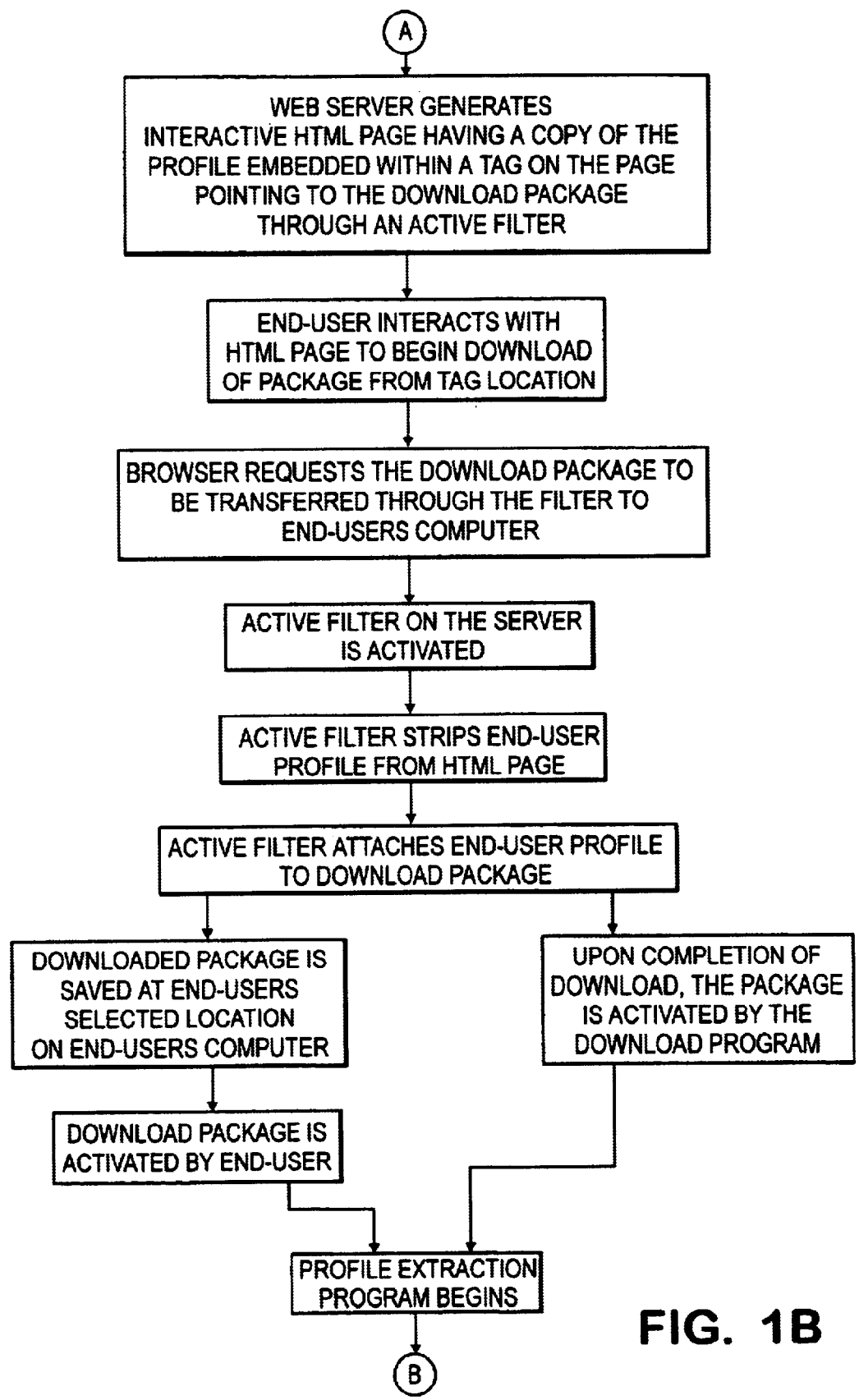
Figure 1C:
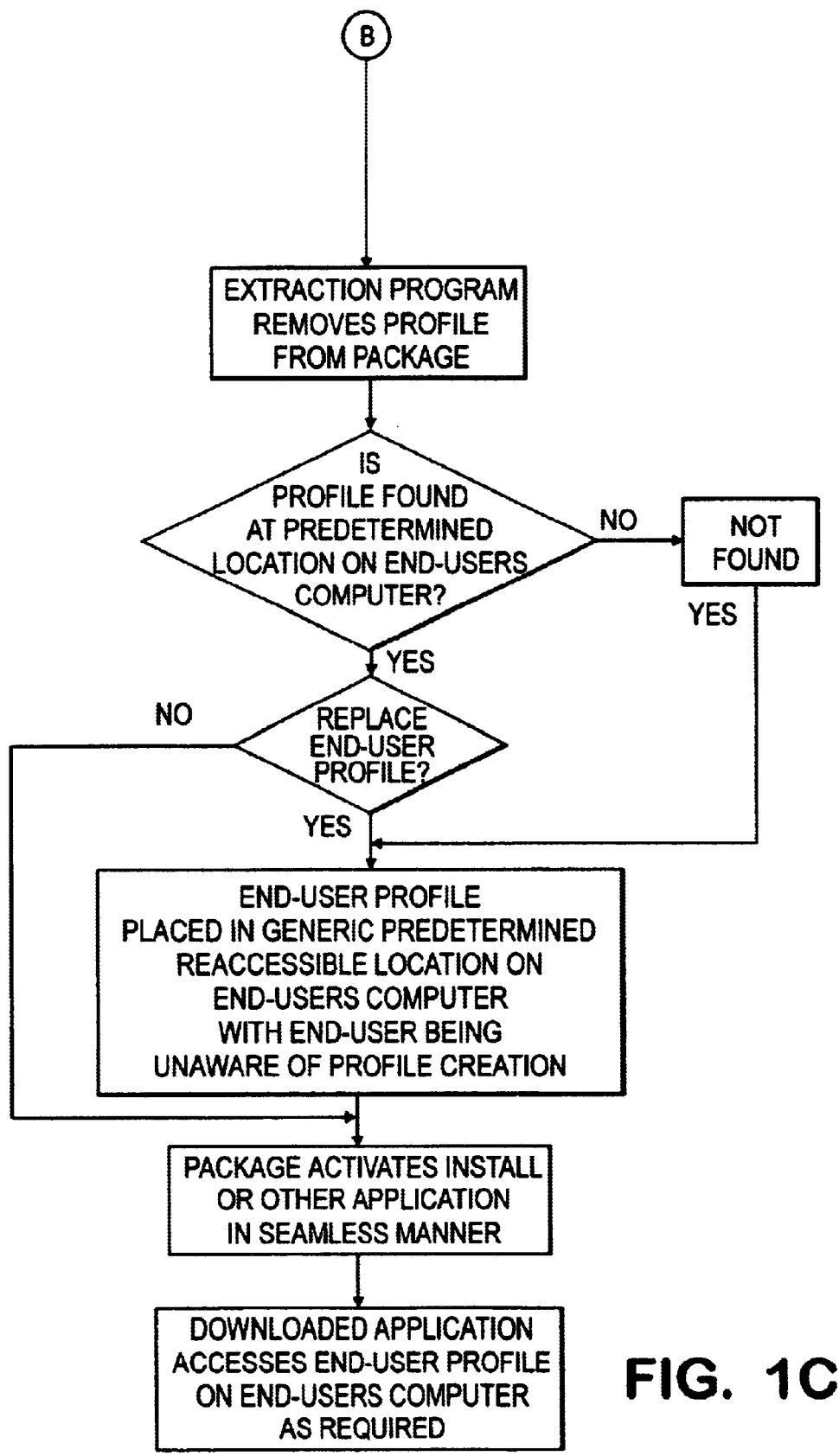

Referring now to the FIGURE in greater detail it will be understood that the method is primarily proposed for use in an HTML based e-commerce environment, where an end user logs onto the internet, looking to purchase or download a program or information (data) from an e-commerce site.

Although this is the primary purpose for which the method was intended when developed, it should not be construed as limiting, inasmuch as application of the method to other environments of use will become obvious upon perusal of the following description.

In the e-commerce environment, an end user logs onto the internet and opens one of several available browsers. The end user then logs onto a desired e-commerce site via the browser.

It will be understood that, typically, information is polled from the user and downloaded onto the computer of the user in a not only browser specific but browser dependent manner, with the most well known form of such informational data storage medium commonly being referred to as a cookie.

The drawbacks of this type of system are first that the cookie or equivalent is only reaccessible when the end user returns to the website using the same browser which generated the cookie and second that programming is available which does not allow such cookie to be stored on the end user's computer.

Thus, either the blocking of cookies can take place or a switch in browsers will defeat the reaccessibility of the end user information or profile, requiring the end user to take time and trouble in re-entering information required by either the e-commerce site, or for example, a program requiring registration for operation thereof.

The incompatibility in information retrieval between the various available browsers was the impetus in developing the present method, to provide a reaccessible end user profile which is not browser specific or browser dependent and which is stored in a generically accessible location on the user's computer, as will be defined hereinafter.

In the method disclosed herein, after the end user logs onto the website, the server of the website determines if a profile for the end user logging on exists on the server. If no end user profile is found to exist, the server can proceed in one of two alternatives.

In the first alternative, the end user is polled for information, such as name, email address, etc., and an end user profile is created from the input information and stored on the server. Then the end user is allowed to choose the desired download.

In the second alternative, the end user first chooses the desired data for downloading, and, once the choice is entered, the server then polls the end user for desired user profile information such as that described above, etc. and the end user profile is then created and stored on the server.

However, if the website server determines that a profile already exists for the end user, the polling does not take place, and no profile is generated, with the end user being able to immediately choose the desired data for download.

Next, the server generates a download package which includes the data that the end user has selected for download and a preexisting profile extraction program for use in extracting the user profile, which will become part of the download package as will be described hereinafter.

The website server also generates an interactive HTML page having a copy of the user profile on the server embedded within a tag on the page, with the tag pointing to the download package through an active filter.

This is all accomplished behind the scenes, so to speak, with the end user merely seeing a DOWNLOAD button appear on the HTML page.

When the end user interacts with the HTML page by "clicking on" (activating) the DOWNLOAD button, downloading onto the user's computer of the download package from the tag location begins.

In this respect, when the DOWNLOAD button is activated by the end user, the browser being used requests the download package to be transferred through the active filter to the end user's computer.

The active filter, a program on the server, now functions to strip the copy of the end user profile from its embedded location on the interactive HTML page and attaches the profile to the download package being transferred therethrough.

Typically, once transference of the download package onto the end user's computer is complete, one of two possible options becomes available.

Under a first option, the end user causes the downloaded package to be saved at a desired location on the computer and then manually initializes (begins installation of the data in) the download package.

Under an alternative option, upon completion of the download onto the end user's computer, the download package is automatically initialized by the download program.

Regardless of which option takes place, upon initializing of the downloaded package, the extraction program of the package is activated to locate and extract the user profile from the download package. The extraction program next determines if a profile is found at a predetermined generic, reaccessible location on the end user's computer.

If the profile is found, it is next determined whether or not the profile is to be replaced.

If the profile is not to be replaced, the package activates an install, or other required application, to make the downloaded data accessible to the end user, with the activated application being able to access the reaccessible end user profile on the end user's computer as required, such as for registration, etc.

Alternatively, if the profile was found and it is desired that replacement thereof should take place, or, if no existing profile was found on the end user's computer, the profile extracted (removed) from the download package is placed in the generic predetermined reaccessible location on the end user's computer, with installation or other application of accessibility of the downloaded data also taking place in a seamless manner. In the preferred embodiment of the method, this location is within the registry of the operating system.

Running of the extraction program is performed in such a seamless manner that the end user is unaware of it functioning, and merely sees that the desired application for accessing the desired data is being installed onto the computer.

The end user profile, having been stored in such generically accessible location, is now available to be reaccessed by the downloaded application as required or by the site server for downloads of any sort, such as upgrades, options, other software, etc., with the returning user being recognized by the site server without need of rekeying any user identification, regardless of which browser the end user should happen to be using to gain access to the site.

It will be understood here that since the most commonly utilized present day operating system is Windows, that the end user profile would preferably be embedded into the Windows registry.

As described above, the method of the present invention provides a number of advantages, some of which have been described above, and others of which are inherent in the invention. Also, modifications may be proposed to the method without departing from the teachings herein. Accordingly the scope of the invention is only to be limited as necessitated by the accompanying claims.

What is claimed is:

1. A method for creating, transmitting, extracting and storing at a predetermined location on an end user's computer, a browser independent reaccessible end user profile at least when an end user first logs onto a website offering desired downloadable data and downloads data therefrom, the method comprising the steps of:

determining if a profile for the end user exists on the website server and if not;

polling the end user and obtaining input desired for creating the profile on the server;

creating a profile;

embedding a copy of the profile into an action tag pointing to a download package through a data filter on the server;

generating a download package comprising the desired data and a profile extraction program;

generating an HTML page including the action tag for actuation by the user for downloading selected data;

upon execution of the action tag by the user beginning operation of the data filter to transfer the user profile from the tag into the download package and downloading the package;

upon opening of the package running the extraction program to extract the profile from the download package and saving the profile to a predetermined file location on the end user's computer.

2. The method of claim 1 wherein the data filter is an active filter.

3. The method of claim 1 wherein the profile is downloaded into the registry of the end user's operating system.

4. The method of claim 1 wherein the profile copy is linked to the package being downloaded upon actuation of a download button provided on the interactive HTML page.

5. The method of claim 1 where in the website server determines if an end user profile exists thereon and upon finding same accesses and reuses the information.

6. The method of claim 1 wherein the website server determines if a user profile exists thereon and upon finding none, begins a process of creating one.

7. The method of claim 1 wherein transfer of the user profile to the user's computer is invisible to the user.

8. The method of claim 1 wherein extraction of the user profile and application installation are simultaneous and performed seamlessly.

9. The method of claim 1 wherein extraction of the profile is invisible to the user.

10. The method of claim 1 wherein placement of the extracted profile at the predetermined generic location on the user's computer is invisible to the user.

11. The method of claim 1 wherein the predetermined generic location is the registry of computer's operating system.

12. The method of claim 2 wherein the active filter comprises a program.

13. Computer executable software process code for creating, transmitting, extracting and storing at a predetermined location on an end user's computer, a browser independent reaccessible end user profile at least when an end user first logs onto a website offering desired downloadable data and downloads data therefrom, the code comprising:

code for determining if a profile for the end user exists on the website server;

code for polling the end user and obtaining input desired for creating the profile on the server;

code for creating the profile;

code for embedding a copy of the profile into an action tag pointing to a download package through a data filter on the server;

code for generating a download package comprising the desired and a profile extraction program;

code for generating the HTML page including the action tag for actuation by the user for downloading selected data;

upon extraction of the action tag by the user, code for beginning operation of the data filter to transfer the user profile from the tag into the download package and downloading the package;

upon opening of the package, code for running the extraction program to extract the profile from the download package and saving the profile to a predetermined file location on the end user's computer.

14. A computer executed process for creating, transmitting, extracting and storing at a predetermined location on an end user's computer, a browser independent reaccessible end user profile at least when an end user first logs onto a website offering desired downloadable data and downloads data therefrom, the process comprising the steps of:

determining if a profile for the end user exists on the website server and if not;

polling the end user and obtaining input desired for creating the profile on the server;

creating the profile;

embedding a copy of the profile into an action tag pointing to a download package through a data filter on the server;

generating a download package comprising the desired data and a profile extraction program;

upon execution of the action tag by the user beginning operation of the data filter to transfer the user profile from the tag into the download package and downloading the package;

upon opening of the package running the extraction program to extract the profile from the download package and saving the profile to a predetermined file location on the end user's computer.

* * * * *